(12) United States Patent  
Tsukuda

(10) Patent No.: US 6,870,147 B1  
(45) Date of Patent: Mar. 22, 2005

(54) LIGHT STABILITY TESTING DEVICE

(75) Inventor: Hiroshi Tsukuda, Takatsuki (JP)

(73) Assignee: Nagano Science Equipment Mfg. Co., Ltd. (JP)

( * ) Notice: Subject to any disclaimer, the term of this patent is extended or adjusted under 35 U.S.C. 154(b) by 75 days.

(21) Appl. No.: 10/363,271

(22) PCT Filed: May 20, 2002

(86) PCT No.: PCT/JP02/04841

§ 371 (c)(1),  
(2), (4) Date: Feb. 28, 2003

(87) PCT Pub. No.: WO03/002983

PCT Pub. Date: Jan. 9, 2003

(30) Foreign Application Priority Data

Jun. 29, 2001 (JP) ........................................ 2001-198878

(51) Int. Cl.⁷ ................................................. G01J 1/36
(52) U.S. Cl. ..................... 250/204; 250/205; 250/216; 250/365; 250/372; 356/213
(58) Field of Search ................................ 250/203, 205, 250/216, 365, 372; 356/213, 222

(56) References Cited

U.S. PATENT DOCUMENTS 5,486,701 A * 1/1996 Norton et al. .............. 250/372  
2003/0052275 A1 * 3/2003 Berger ....................... 250/372

FOREIGN PATENT DOCUMENTS

| JP | 204424 | 12/1982 |
| JP | 218407 | 12/1984 |
| JP | 157647 | 10/1988 |
| JP | 72116 | 3/1993 |
| JP | 20036 | 1/1995 |
| JP | 33826 | 2/1997 |
| JP | 132938 | 5/1999 |
| JP | 13587 | 1/2001 |
| JP | 3173357 | 3/2001 |

* cited by examiner

Primary Examiner—Stephone B. Allen  
Assistant Examiner—Patrick J. Lee  
(74) Attorney, Agent, or Firm—Howson and Howson

(57) ABSTRACT

A light stability testing device for conducting an accurate light stability test that permits an accurate ultraviolet irradiation and an accurate visible light irradiation, the device comprising an optical sensor having a visible light measuring sensor (5) for measuring the dose of visible light, and a ultraviolet measuring sensor (6) for measuring the dose of ultraviolet ray, an optical system having a total light regulating means (331) for regulating the absolute quantity of light emitted from a light source and a ultraviolet ray regulating means (335) for regulating the dose of ultraviolet ray in light regulated by the total light regulating means, and a control unit for controlling a total light control unit that controls the total light regulating means (331) by a signal from a visible light measuring sensor (5), and the ultraviolet ray regulating means (335) by a signal from the ultraviolet measuring sensor (6).

19 Claims, 9 Drawing Sheets

LIGHT STABILITY TESTING DEVICE

FIELD OF THE INVENTION

The present invention relates to a light stability testing device for testing light stability of drugs, for example.

BACKGROUND OF THE INVENTION

Conventional light stability testing devices will be described with reference to FIG. 8, FIG. 9, FIG. 10, and FIG. 11.

FIG. 8 is a front view showing the main part of a first light stability testing device according to a prior art. This light stability testing device 1 regulates light rays emitted from a light source 2 by an optical system 3, irradiates the same onto a sample (unillustrated) placed on a sample stage, thereby testing light stability of the sample. The optical system 3 is composed mainly of a first reflecting mirror 31, a light regulating means 33, an integrated lens 35 as a light flux control means, a second reflecting mirror 37, and a third reflecting mirror 39. For the integrated lens 35, chalk-like quartz sticks are bundled and a spherical glass is adhered to the top. When light rays pass therethrough, each quartz column behaves like a small light source. Thereby, even if, for example, a light flux after passing through an appointed diaphragm is rectangular, this light flux can be changed to a circular light flux.

4 denotes a sample stage for placement of a sample (unillustrated), and to this sample stage 4, a visible light measuring sensor 5 for measuring the dose of visible light and an ultraviolet measuring sensor 6 for measuring the dose of ultraviolet rays are attached. Herein, the sample stage 4 is rotatable by driving force of a drive unit 7 via a rotation axis 71.

This first light stability testing device 1 according to the prior art is divided broadly into a lamp house 8 and a sample chamber 9, and in the above-described construction, the light source 2 and the first reflecting mirror 31, light regulating means 33, integrated lens 35 as a light flux control means 35, and second reflecting mirror 37 of the optical system 3 are installed in the lamp house 8, while the third reflecting mirror 39 and sample stage 4 of the optical system 3 are installed in the sample chamber 9.

FIG. 9 shows a first light stability testing device 1 having the above-described construction in detail. Namely, the light regulating means 33 included in the optical system 3 comprises a diaphragm as a total light regulating means 331 and an ultraviolet limit filter as an ultraviolet regulating means 333. The diaphragm as a total light regulating means 331 uniformly regulates and controls the quantity of all light rays of visible light and ultraviolet rays, and the ultraviolet limit filter as an ultraviolet regulating means 333 controls only ultraviolet rays (in particular, far ultraviolet rays) of light rays. 91 denotes an entrance window made of quartz glass, which is provided for the sample chamber 9. Herein, as the light source 2, a xenon lamp is used.

In the first light stability testing device 1 having the above-described construction, first, a sample (unillustrated) is placed on the sample stage 4. Then, light rays are emitted from the xenon lamp of the light source 2. These light rays are first converged by the first reflecting mirror 31, and then pass through the ultraviolet limit filter as an ultraviolet regulating means 333 for control of ultraviolet rays. Then, the light rays are passed through the diaphragm as a total light regulating means 331 for regulation and control of the total quantity of light, that is, the quantity of all light rays of visible light and ultraviolet rays. Then, the light ray direction is regulated by the integrated lens 35 as a light flux control means. Then, the light ray direction is changed to approximately horizontal, and the light rays enter the sample chamber 9 through the quartz glass entrance window 91, and furthermore, the light rays are reflected downward by the third reflecting means 39 and irradiated onto a sample (unillustrated) placed on the sample stage 4. Since irradiation is carried out for a long time, for an improvement in irradiation distribution, the sample stage 4 is rotated by the drive unit 7 via the rotation axis 71 during the irradiation, whereby light stability of the sample is tested.

In addition, during the above-described irradiation, a signal from either visible light measuring sensor 5 or ultraviolet measuring sensor 6 is transmitted to a control unit (unillustrated), and based on computing by this control unit, the quantity of light rays and time are controlled.

On the other hand, FIG. 10 is a front view showing a main part of a second light stability testing device according to a prior art. Unlike the above-described first light stability testing device, this second light stability testing device 1 uses fluorescent lamp-like tubular light sources as light sources 2, has no large scale optical system, and simply has a reflecting mirror 31. In other words, in this second light stability testing device 1, light rays emitted from the light sources 2 are directly irradiated onto a sample. 333 denotes a stationary ultraviolet regulating means, which is for regulation of the quantity of ultraviolet rays from the light sources.

5 denotes a visible light measuring sensor, 6 denotes an ultraviolet measuring sensor, and these are attached to a sample stage 4. The sample stage 4 is rotatable by driving force of a drive unit 7 via a rotation axis 71.

During irradiation, the quantity of light from the light sources 2 are regulated based on a signal from the visible light measuring sensor 5. In addition, values measured by the ultraviolet measuring sensor 6 are integrated and recorded.

However, in the above-described light stability testing devices 1 according to the prior arts, the following problems have existed.

FIG. 11 is a diagram showing spectrum distributions of sunlight, a xenon lamp, and a D65 lamp (TOSHIBA FLR20S and DEDL-D65/M). The horizontal axis indicates a wavelength, and the longitudinal axis indicates a relative value of intensity. As shown in FIG. 11, spectrum distributions of light sources which approximate sunlight, such as, a xenon lamp and a D65 lamp have excessive ultraviolet parts compared to the spectrum distribution of sunlight. In general, visible light is in a range of 380 nm to 780 nm and is visible to human eyesight. Ultraviolet rays have a wavelength from 200 nm to 380 nm and are, therefore, invisible to the naked eye. Strictly, this wavelength range is called a near-ultraviolet range, and a range from 100 nm to 200 nm is called a far-ultraviolet range (Toshiharu Tako, Junpei Tsujiuchi, Shigeo Minami (eds.), "Light Measurement Handbook," 2nd ed. published Jan. 20, 1997, p. 572).

On the other hand, criteria of the Ministry of Welfare for a light stability test of a drug, etc., of a sample have been provided based on sunlight, and concretely, an integrated dose has been provided as 1200 kLxhr or more for visible light, and for ultraviolet rays, as 200 whr/m$^2$ or more.

Accordingly, in the light stability testing unit 1 according to the prior art, with respect to the light source 2 having excessive ultraviolet rays such as a xenon lump, the ultraviolet limit filter as an ultraviolet regulating means 333 is a stationary type and sets the quantity of ultraviolet rays to approximately the above-described prescribed value.

However, a light stability test extends for a long time, and for example, if an instantaneous irradiation value of 1000 Lx is selected, it extends for no less than 1200 hours. Accordingly, a deterioration in the light source 2 and the optical system 3 occurs with an elapse of time. Moreover, this tendency to deteriorate is greater in the ultraviolet part than in the visible light part, therefore, if a light-reducing value of the ultraviolet limit filter as the ultraviolet regulating means 333 has been designed for the lowest dose, ultraviolet rays are likely to become insufficient when visible light reaches 1200 kLxhr, and as a result, an accurate light stability test cannot be conducted, therein a problem exists.

On the other hand, in the aforementioned second light stability testing device, deteriorating tendencies of the light sources 2, etc., are different among the plurality of light sources 2 and cannot be easily estimated. Accordingly, the dose is usually set to a slightly excessive dose, and when the integrated dose of visible light reaches 1200 kLxhr, ultraviolet rays may reach 220–280 whr/m$^2$ if the light sources 2 are new. In actuality, in terms of a sample such as a drug, an influence of ultraviolet rays thereon is often greater, and as a result, an accurate light stability test cannot be conducted, therein a problem exists.

Therefore, the present invention has been made to solve the above-described problems and an object thereof is to provide a light stability testing device which enables an accurate ultraviolet irradiation and an accurate visible light irradiation, and thus can conduct an accurate light stability test.

SUMMARY OF THE INVENTION

In order to achieve the above object, according to the present invention, a light stability testing device comprises: a light source; an optical system for regulating light rays emitted from this light source; a sample stage for placement of a sample onto which light rays passed through this optical system are to be irradiated; a light measuring sensor for measuring the dose of light rays, attached to this sample stage; and a control unit to which a signal from this light sensor is transmitted and which controls the optical system, wherein the light sensor comprises a visible light measuring sensor for measuring the dose of visible light and an ultraviolet measuring sensor for measuring the dose of ultraviolet rays, the optical system comprises a total light regulating means for regulating the absolute quantity of light rays emitted from the light source and an ultraviolet regulating means for regulating the dose of ultraviolet rays of light rays, and the control unit comprises a total light control portion for controlling the total light regulating means by a signal from the visible light measuring sensor and an ultraviolet control portion for controlling the ultraviolet regulating means by a signal from the ultraviolet measuring sensor. Herein, the "absolute quantity of light rays" is a total dose of all the visible light and ultraviolet rays.

In addition, it is preferable that the optical system comprises a total light regulating means for regulating the absolute quantity of light rays emitted from the light source and an ultraviolet regulating means for regulating the dose of ultraviolet rays of light rays emitted from this total light regulating means.

In addition, it is preferable that the optical system comprises a light ray sorting means for differentiating a course of ultraviolet rays from a course of visible light and a light ray merging means for merging ultraviolet rays with visible light, and the ultraviolet regulating means regulates the dose of ultraviolet rays passed through the light ray sorting means.

In addition, it is preferable that the light ray sorting means is a dichroic mirror.

In addition, it is preferable that the light ray merging means is a dichroic mirror.

In addition, it is preferable that the total light regulating means comprises a plurality of movable filters.

In addition, it is preferable that the plurality of filters are two filters and symmetrically movable.

In addition, it is preferable that the optical system comprises a light flux control means for controlling a light flux of light rays.

In addition, it is preferable that the light flux control means is an integrated lens.

In addition, it is preferable that the ultraviolet regulating means is provided at a position to regulate the dose of ultraviolet rays of light rays passed through the light flux control means.

Furthermore, according to the present invention, a light stability testing device comprises: a light source; a sample stage for placement of a sample onto which light rays emitted from this light source are to be irradiated; a light sensor for measuring the dose of light rays, attached to this sample stage; and a control unit to which a signal from this light sensor is transmitted and which controls the light source, wherein the light source comprises excessive ultraviolet light sources and insufficient ultraviolet light sources. The "excessive ultraviolet light source" means a light source with a greater ultraviolet component compared to that of sunlight, and the "insufficient ultraviolet light source" is a light source having a smaller ultraviolet component compared to that of sunlight.

In addition, it is preferable that the light sensor comprises a visible light measuring sensor for measuring the dose of visible light and an ultraviolet measuring sensor for measuring the dose of ultraviolet rays, an ultraviolet regulating means for regulating the dose of ultraviolet rays of light rays emitted from the light source is provided between the light source and sample stage, and the control unit comprising a light source control portion for controlling the light source by a signal from the visible light measuring sensor and an ultraviolet control portion for controlling the ultraviolet regulating means by a signal from the ultraviolet measuring sensor. In addition, it is preferable that the light sensor comprises a visible light measuring sensor for measuring the dose of visible light and an ultraviolet measuring sensor for measuring the dose of ultraviolet rays, the control unit comprises an insufficient ultraviolet light source control portion for controlling the insufficient ultraviolet light sources by a signal from the visible light measuring sensor and an excessive ultraviolet light source control portion for controlling the excessive ultraviolet light sources by a signal from the ultraviolet measuring sensor.

In addition, it is preferable that control in the light source control portion is performed by flashing control through inverter light control of the light source.

In addition, it is preferable that control in the light source control portion is performed by flashing control through phase control of the light source.

In addition, it is preferable that the sample stage is rotatable.

In addition, it is preferable that small rotatable sample stages are provided on the sample stage.

In addition, it is preferable that a rotation rate between the sample stage and small sample stages is 7 or more. In addition, it is preferable that, for control in the control unit, provided is a corrective control portion which corrects an instantaneous irradiation value of a signal concerning irradiation from the light sensor while taking an integrated irradiation value into consideration.

BRIEF DESCRIPTION OF THE DRAWINGS

FIG. 7($b$) is a diagram showing a phase control method; and FIG. 7($c$) is a diagram showing a relatively long-timed ON/OFF control method.

DETAILED DESCRIPTION OF THE PREFERRED EMBODIMENTS

Embodiments of the present invention will be described based on examples, with reference to the drawings.

Figure 1:
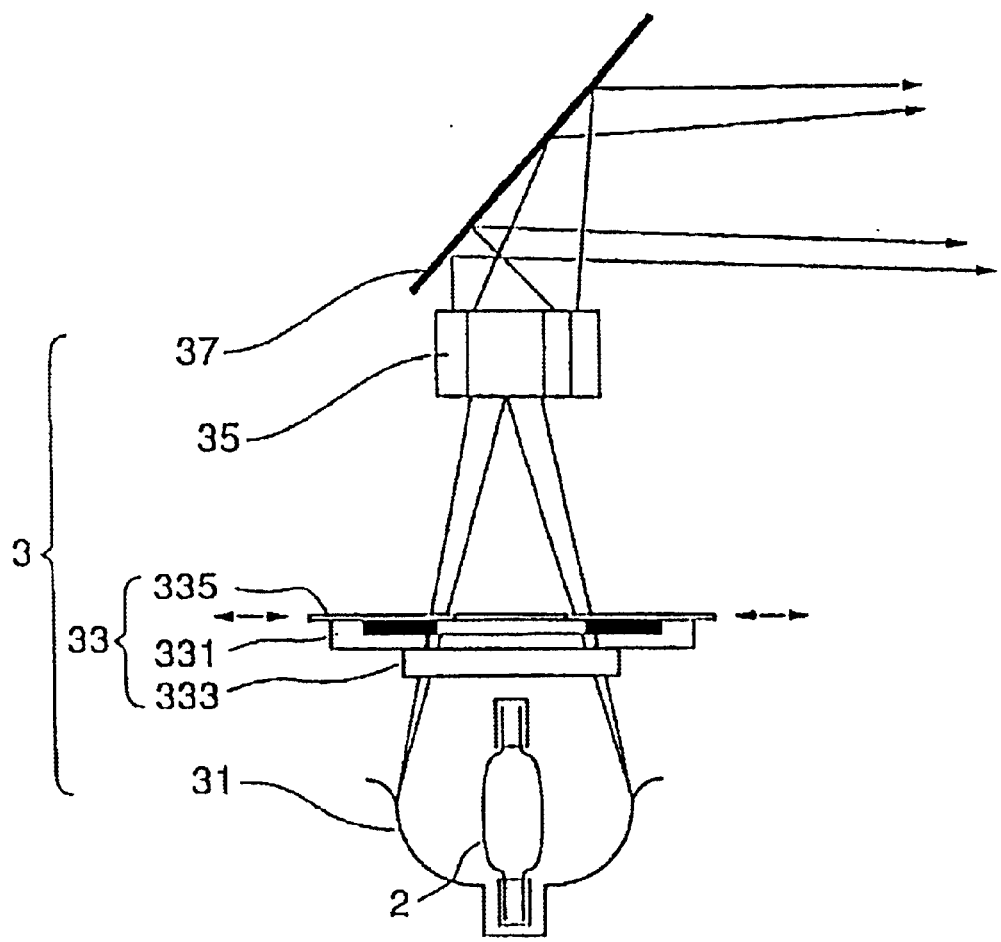
FIG. 1 is a front view showing a main part of the light source and optical system of the light stability testing device according to the first example of the present invention.

Now, a first example of the present invention will be described with reference to FIG. 1, FIG. 2, and FIG. 3. FIG. 1 is a front view showing a main part of a light source and an optical system of a light stability testing device according to the first example of the present invention, FIG. 2 is a perspective view showing a main part of a movable ultraviolet regulating means in an optical system of a light stability testing device according to the first example of the present invention, FIG. 3 is a perspective view showing a main part of a sample stage of a light stability testing device according to the first example of the present invention.

2 denotes a light source, 31 denotes a first reflecting mirror, and 33 denotes a light regulating means, which is composed mainly of a movable ultraviolet regulating means 335, a stationary ultraviolet regulating means 333, and a movable total light regulating means 331. 35 denotes an integrated lens as a light flux control means, and 37 denotes a second reflecting mirror. The stationary ultraviolet regulating means 333 mainly regulates far ultraviolet rays, while the movable ultraviolet regulating means 335 mainly regulates near ultraviolet rays.

Figure 2:
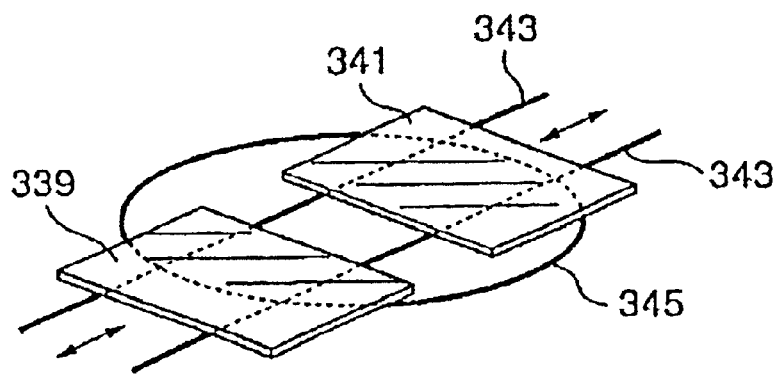
FIG. 2 is a perspective view showing a main part of the ultraviolet regulating means in the optical system of the light stability testing device according to the first example of the present invention.
Figure 3:
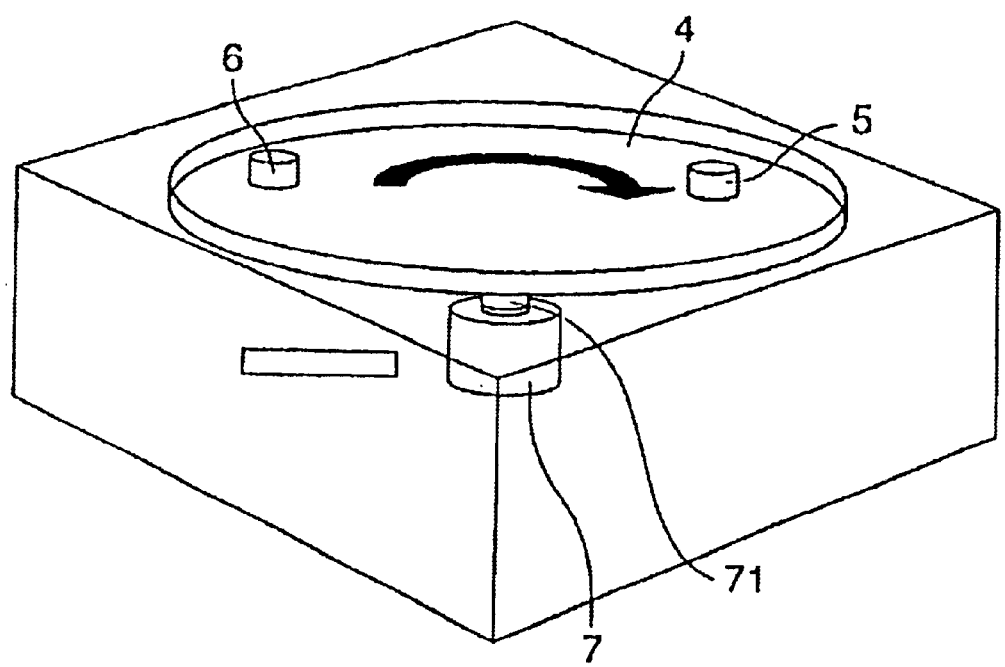
FIG. 3 is a perspective view showing a main part of the sample stage of the light stability testing device according to the first example of the present invention.

As shown in FIG. 2, in the movable ultraviolet regulating means 335, two parallel rails 343 and 343 are provided on a light course 345, and on these rails 343 and 343, filters 339 and 341 are symmetrically movable. In other words, the filters 339 and 341 can respectively move so as to mutually approximate and separate on the rails 343. Moreover, the movable total light regulating means 311 also has similar principles and constructions.

In addition, a control unit (unillustrated) comprises a total light control portion for controlling the movable total light regulating means 331 by a signal from a visible light measuring sensor 5 provided on a sample stage 4 and an ultraviolet control portion for controlling the movable ultraviolet regulating means 335 by a signal from an ultraviolet measuring sensor 6.

Now, operations and effects of the light stability testing device according to the first example of the present invention having the above-described construction will be described.

First, a sample is placed on the sample stage 4, light rays emitted from the light source 2 are regulated by the optical system 3 and then irradiated onto the sample. During irradiation, for an improvement in irradiation distribution, the sample stage is rotated by a drive unit 7 via a rotation axis 71.

Light rays emitted from the light source 2 are converged by the first reflecting mirror 31. Then, far ultraviolet rays are controlled and regulated by the stationary ultraviolet regulating means 333. Then, the total quantity of light, that is, the quantity of visible light and the quantity of ultraviolet rays are controlled by the total light regulating means 331. This total light regulating means 331 is controlled and regulated by a signal from the visible light measuring sensor 5 provided on the sample stage 4.

The light rays regulated by the total light regulating means 331 are controlled by the movable ultraviolet regulating means 335. In other words, by a signal from the ultraviolet measuring sensor 6 provided on the sample stage 4, the quantity of ultraviolet rays is controlled and regulated based on opening and closing of the filters 339 and 341 on the rails 343.

Concretely, the filters 339 and 341 are moved so as to shade $\alpha$ % of the light course 345. In FIG. 2, oblique-line areas of the filters 339 and 341 are shaded. In this case, if filters 339 and 341 having an ultraviolet transmittance $\beta$ % are used, ultraviolet rays are transmitted 100% as (100-$\alpha$)% of the quantity of light rays, while $\alpha$ % of the quantity of light rays results in a transmittance $\beta$ %. Accordingly, an ultraviolet transmittance as a whole becomes as follows.

Ultraviolet transmittance=(100-$\alpha$)+$\alpha\beta$/100
=100-(100-$\alpha$) $\alpha$/100 [%]

As such, the ultraviolet transmittance becomes variable from 100% to $\beta$ %. Namely, where $\alpha$=100, the ultraviolet transmittance results in $\beta$ %, and where $\alpha$=0, the ultraviolet transmittance results in 100%. For instance, in the present example in that the light source 2 is a xenon lamp, the ultraviolet component is slightly less than approximately 3 times an appointed reference value. Accordingly, if a filter with $\beta$=30% is used, the ultraviolet component becomes approximately equal to the appointed reference value. After consideration of these factors, in a manner where the movable total light regulating means 331 is controlled by the total light control portion (unillustrated) by use of a signal from the visible light measuring sensor 5 provided on the sample stage 4 and the movable ultraviolet regulating means 335 is controlled by the ultraviolet control portion (unillustrated) by use of a signal from the ultraviolet measuring sensor 6, the dose is finely regulated. As a result, a light stability test which is more accurate than that of the prior art can be conducted.

In the above-described light stability testing device according to the first example, although the movable ultraviolet regulating means 335 has been provided on the total light regulating means 331, it may also be possible to provide the movable ultraviolet regulating means 335 on the integrated lens of a light flux control means 35.

Figure 4:
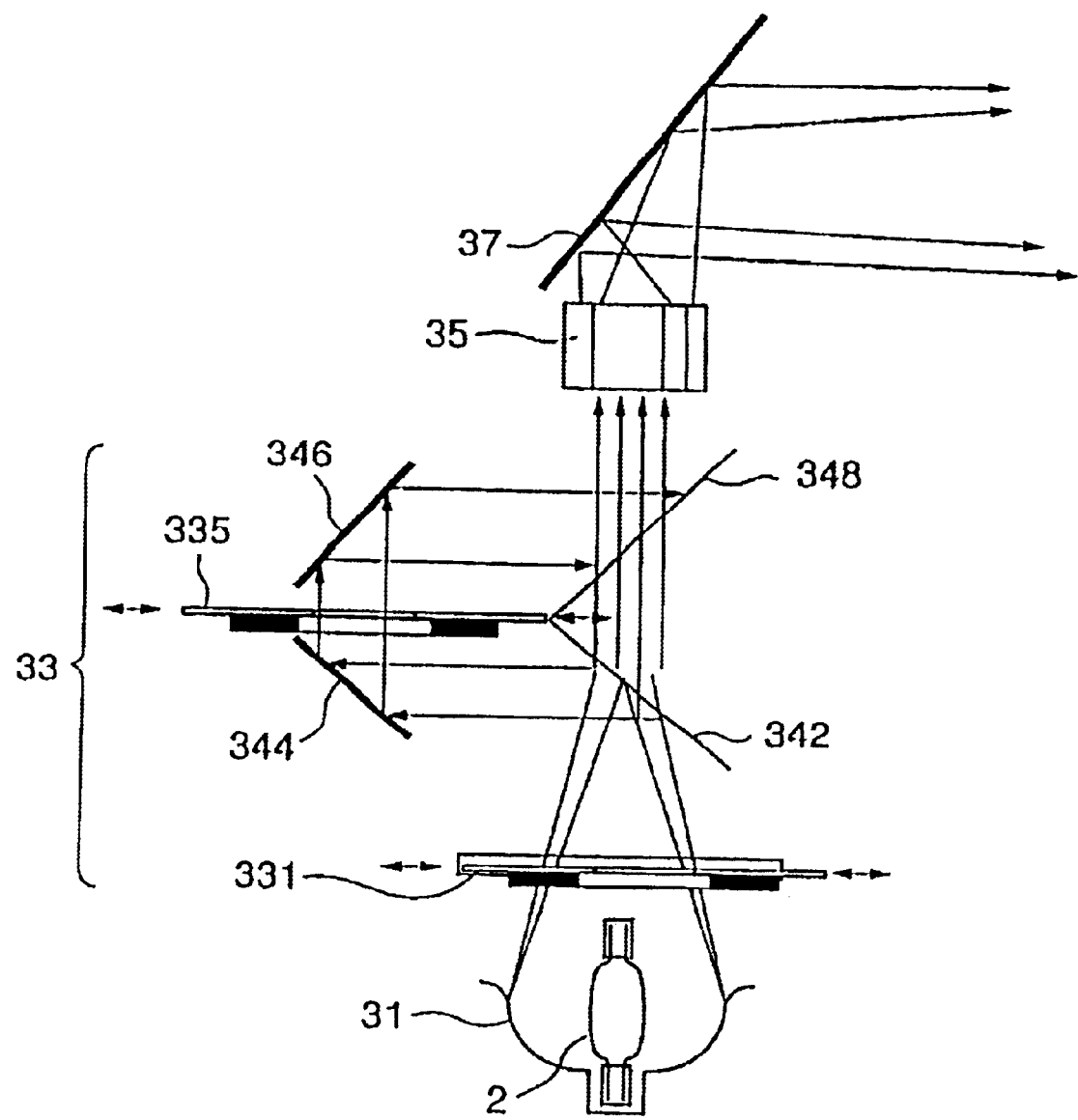
FIG. 4 is a front view showing a main part of the optical system of the light stability testing device according to the second example of the present invention.

Next, a light stability testing device according to a second example of the present invention will be described with reference to FIG. 4. FIG. 4 is a front view showing a main part of an optical system of a light stability testing device according to the second example of the present invention. In comparison with the above-described first example of the present invention, features of this light stability testing device according to the second example exist in that, in a light regulating means 33 included in an optical system thereof, the quantity of ultraviolet rays is regulated in a condition where a movable ultraviolet regulating means 335 is structurally separated from a total light regulating means 331 and an ultraviolet course is made different from a visible light course.

To make the ultraviolet course different from the visible light course, dichroic mirrors 342 and 348 as a light ray sorting means and a light ray merging means are provided in the light regulating means 33. These dichroic mirrors 3.42 and 348 are for sorting light rays based on an appointed reference wavelength, and these dichroic mirrors 342 and 348 operate, in the present example, so as to allow visible light to pass, but so as to reflect ultraviolet rays. By this dichroic mirror 342, only ultraviolet rays of light rays are changed in terms of its course. 344 and 346 denote a fourth reflecting mirror and a fifth reflecting mirror, respectively, which are used to reflect ultraviolet rays.

335 denotes a movable ultraviolet regulating means, whose construction is similar to that of the above-described first example.

Now, operations and effects of the light stability testing device according to the second example of the present invention having the above-described construction will be described.

Light rays emitted from the light source 2 are converged by a first reflecting mirror 31. Then, all light rays, namely, all visible light and ultraviolet rays are regulated and controlled by a movable total light regulating means 331. In other words, similar to the above-described first example, the quantity of all light rays is regulated and controlled based on a signal of a visible light measuring sensor attached to a sample (unillustrated).

Of the light rays passed through the movable total light regulating means 331, only ultraviolet rays are reflected by a dichroic mirror 342 as a light ray sorting means in an approximate 90° direction, and visible light proceeds straight without change. The ultraviolet rays reflected in an approximate 90° direction by the dichroic mirror 342 as a light ray sorting means are reflected by a fourth reflecting mirror 344 by approximately 90° and when the ultraviolet rays pass through a movable ultraviolet regulating means 335, the quantity of ultraviolet rays is controlled. In other words, similar to the above-described first example, the quantity of ultraviolet rays is regulated and controlled based on a signal from an ultraviolet measuring sensor attached to a sample stage (unillustrated).

Then, ultraviolet rays which have passed through the movable regulating means 335 are reflected in an approximate 90° direction by a fifth reflecting mirror 346 and are merged with visible light by a dichroic mirror 348 as a light ray merging means. In other words, ultraviolet rays are reflected in an approximate 90° direction by the dichroic mirror 348 as a light ray sorting means, are made parallel to visible light passed through the dichroic mirror 342, and are merged therewith.

Then, the light flux is formed into a perfect circle shape by an integrated lens 35 as a light flux control means, and the light flux is made incident into a sample chamber by a second reflecting mirror 37 and is irradiated onto a sample, and constructions and operations thereof are similar to those of the light stability testing device according to the aforementioned first example.

As such, in the light stability testing device according to the second example of the present invention, since the quantity of ultraviolet rays is regulated, in the light regulating means 33, in a condition where the movable ultraviolet regulating means 335 is separated from the total light regulating means 331 and the ultraviolet course is made different from the visible light course, further accurate control of the quantity of ultraviolet rays becomes possible, thus light stability of the sample can be further accurately measured.

Figure 5:
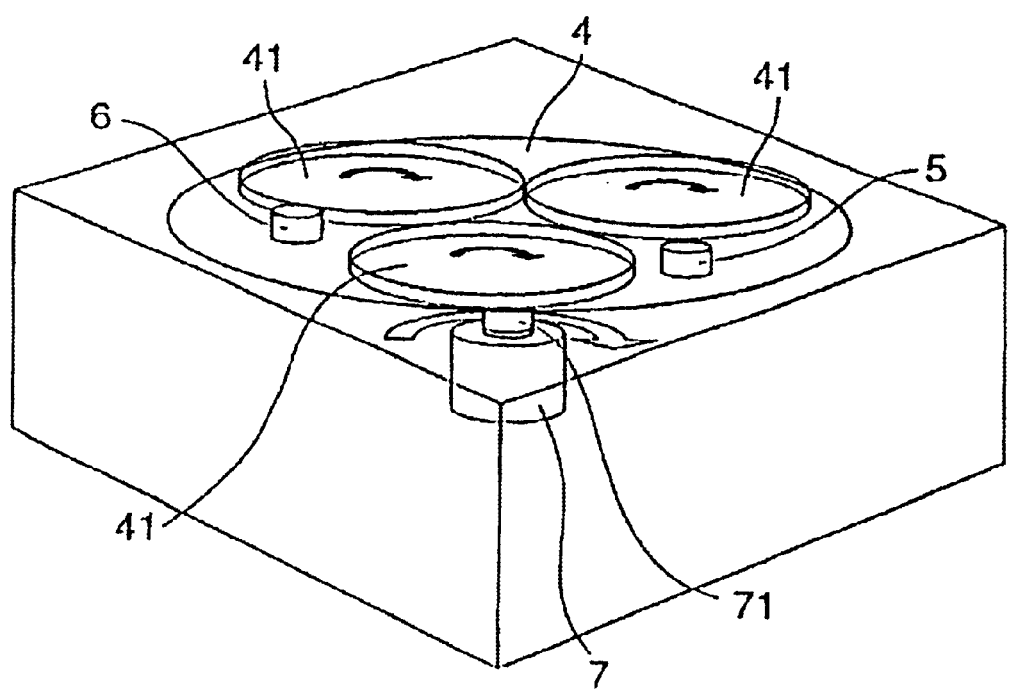
FIG. 5 is a front view showing a main part of the sample stage of the light stability testing device according to the third example of the present invention.

According to the above-described aspects according to the first example and second example of the present invention, since movable filters are used as the total light regulating means and the ultraviolet regulating means, it is necessary to further accurately control the uniformity of light distribution. Therefore, it may also be possible to provide such a sample stage as shown in FIG. 5. FIG. 5 is a front view showing a main part of a sample stage of a light stability testing device according to a third example of the present invention. As such, it is useful to provide three small sample stages 41 on a sample stage 4 and to construct the respective small sample stages 41 so as to be rotatable. As a result, by rotation of the small sample stages 41 along with the rotation of the sample stage 4 by driving force of a drive unit 7 via a rotation axis 71, uniformity of light distribution can be improved. In this case, samples placed on the small sample stages 41 follow so-called epicycloid curves, and in particular, a rotation ratio of 7 or more is effective.

In the examples as mentioned above, for the optical systems, an optical system comprising a movable total light regulating means for regulating the absolute quantity of light rays emitted from the light source and a movable ultraviolet regulating means for regulating the dose of ultraviolet rays of the light rays regulated by this movable full light regulating means has been employed, however, depending on the conditions, it may also be possible to regulate the absolute quantity of light rays by regulating light rays passed through a movable ultraviolet regulating means by use of a movable total light regulating means.

Figure 6:
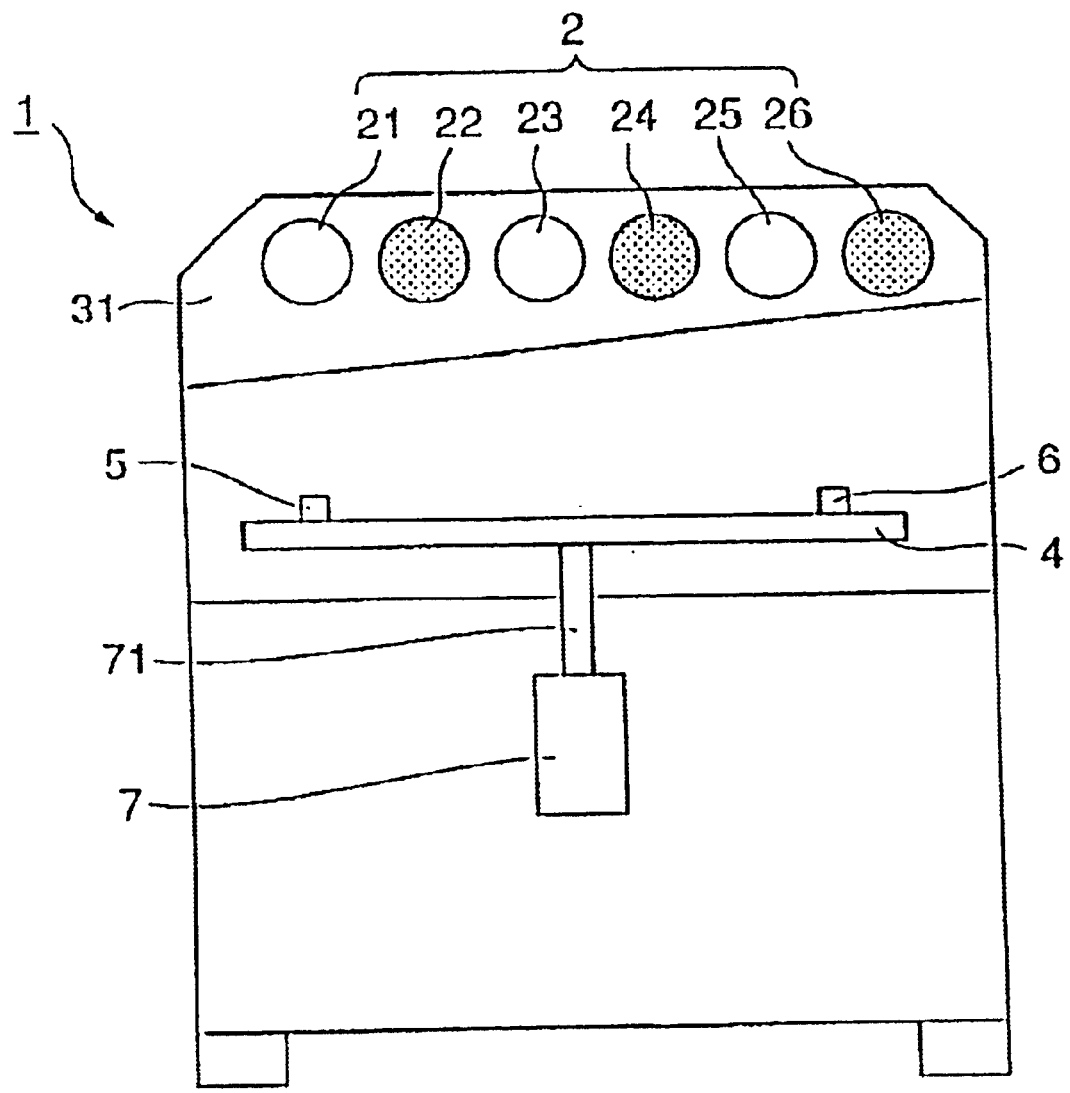
FIG. 6 is a front view showing a main part of the light stability testing device according to the fourth example of the present invention.

A light stability testing device according to a fourth example of the present invention will be described with reference to FIG. 6. FIG. 6 is a front view showing a main part of a light stability testing device according to the fourth example of the present invention.

Unlike the light stability testing devices according to the above-described first and second examples of the present invention, this light stability testing device 1 according to the fourth example of the present invention uses fluorescent lamp-like tubular light sources as a light source 2, has no large scale optical system, and simply has a reflecting mirror 31. In other words, in this second light stability testing device 1 according to the fourth example 4, light rays emitted from the light source 2 are directly irradiated onto a sample.

5 denotes a visible light measuring sensor, 6 denotes an ultraviolet measuring sensor, and these are attached to a sample stage 4. The sample stage 4 is rotatable by driving force of a drive unit 7 via a rotation axis 71.

The light source 2 is composed of six light sources, wherein 21, 23, and 25 denote insufficient ultraviolet light sources, and 22, 24, and 26 are excessive ultraviolet light sources, respectively. In the present example, as insufficient ultraviolet light sources, white luminescent lamps are used, and as excessive ultraviolet light sources, D65 lamps are used. Of these, the insufficient ultraviolet light sources 21, 23, and 25 are controlled by a signal from the visible light measuring sensor 5, and the excessive ultraviolet light sources 22, 24, and 26 are controlled by a signal from the ultraviolet measuring sensor 6. In other words, a control unit (unillustrated) comprises an insufficient ultraviolet light source control portion for controlling the insufficient ultraviolet light sources 21, 23, and 25 by a signal from the visible light measuring sensor 5 and an excessive ultraviolet light source control portion for controlling the excessive ultraviolet light sources 22, 24, and 26 by a signal from the ultraviolet measuring sensor 6. 31 denotes a first reflecting means for reflecting light rays.

Now, operations and effects of the light stability testing device 1 according to the fourth example of the present invention having the above-described construction will be described.

First, a sample (unillustrated) is placed on the sample stage 4. Then, the sample stage 4 is rotated by driving force of a drive unit 7 via a rotation axis 71. During rotation of the sample stage 4, light rays emitted from the light source 2 are directly irradiated onto the sample or light rays reflected by the first reflecting mirror 31 are irradiated onto the sample. At this time, the insufficient ultraviolet light sources 21, 23, and 25 are controlled by the insufficient ultraviolet control portion (unillustrated) by use of a signal from the visible light measuring sensor 5, and the excessive ultraviolet light sources 22, 24, and 26 are controlled by the excessive ultraviolet light source control portion (unillustrated) by use of a signal from the ultraviolet measuring sensor 6.

Through this test, concrete doses resulted as follows.

|  | Instantaneous value | Integrated value |
| --- | --- | --- |
| Visible light | 10001 x | 1200 klxhr |
| Ultraviolet rays | 16–17 μw/cm$^2$ | 200 whr/m$^2$ |

From the above experimental results, it can be understood that an accurate irradiation, that is, an accurate light stability test could be conducted.

Moreover, in the present example, results when no control was performed are as follows.

|  | Instantaneous value | Integrated value |
| --- | --- | --- |
| Visible light | 10001 x | 1200 klxhr |
| Ultraviolet rays | 21–22 μw/cm$^2$ | 258 whr/m$^2$ |

As such, although the quantity of ultraviolet rays was slightly increased, practicability existed.

Figure 10:
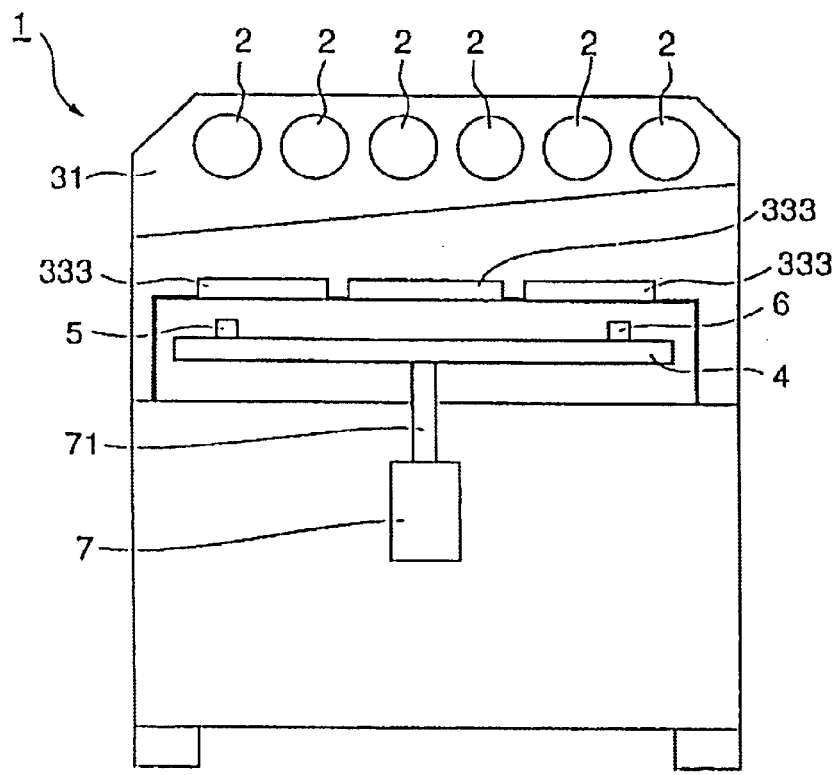
FIG. 10 is a front view showing a main part of the second light stability testing device according to the prior art.
Figure 11:
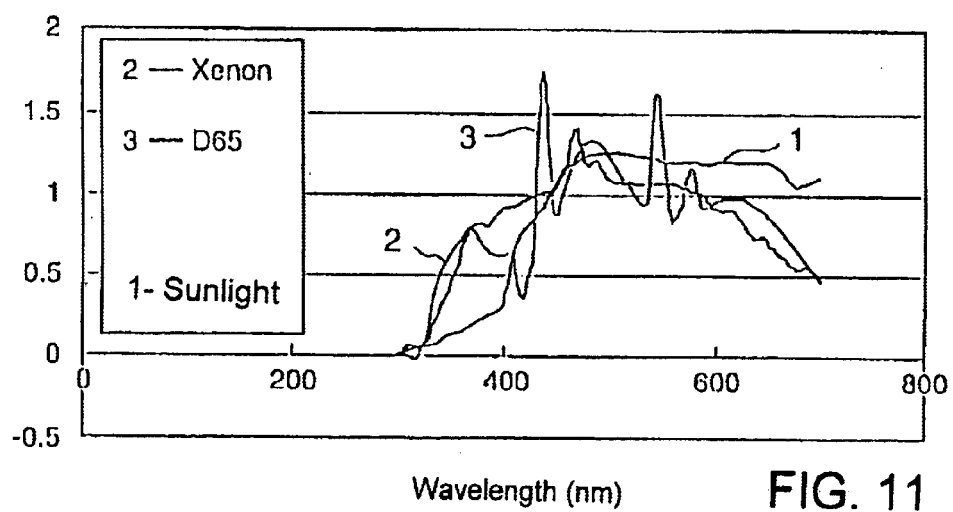
FIG. 11 is a diagram showing spectrum distributions of sunlight, a xenon lamp, and a D65 lamp.

In addition, in the present example, although the excessive ultraviolet light sources 22, 24, and 26 are controlled by the excessive ultraviolet light source control portion (unillustrated) by use of a signal from the ultraviolet measuring sensor 6, it may also be possible to provide movable ultraviolet regulating means at positions 333 of FIG. 10, that is, between the light sources 2 and sample stage 4 and to control these movable ultraviolet regulating means by a signal from the ultraviolet measuring sensor 6.

Figure 7A:
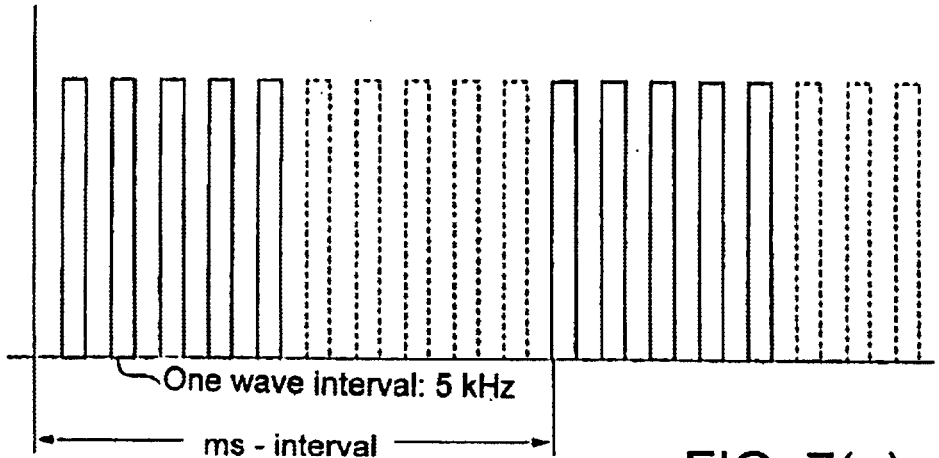
FIG. 7($a$) is a diagram showing an inverter light control method.
Figure 7B:
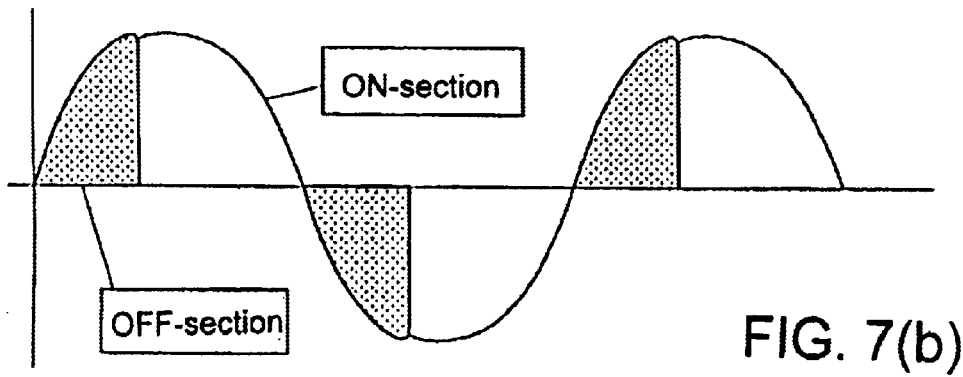
Figure 7C:
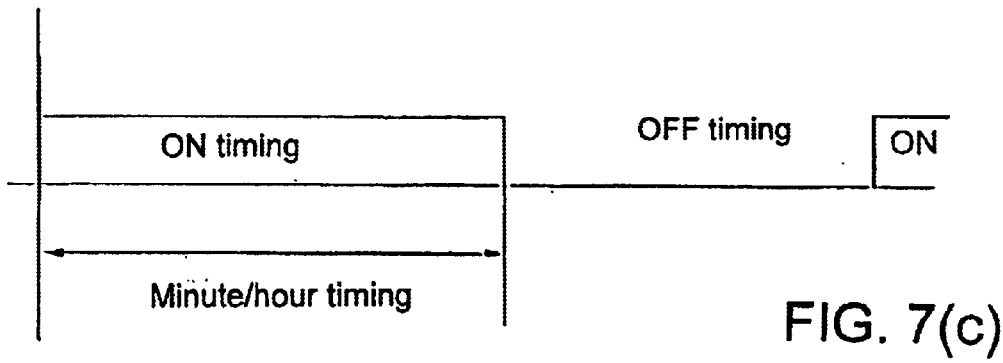
Figure 8:
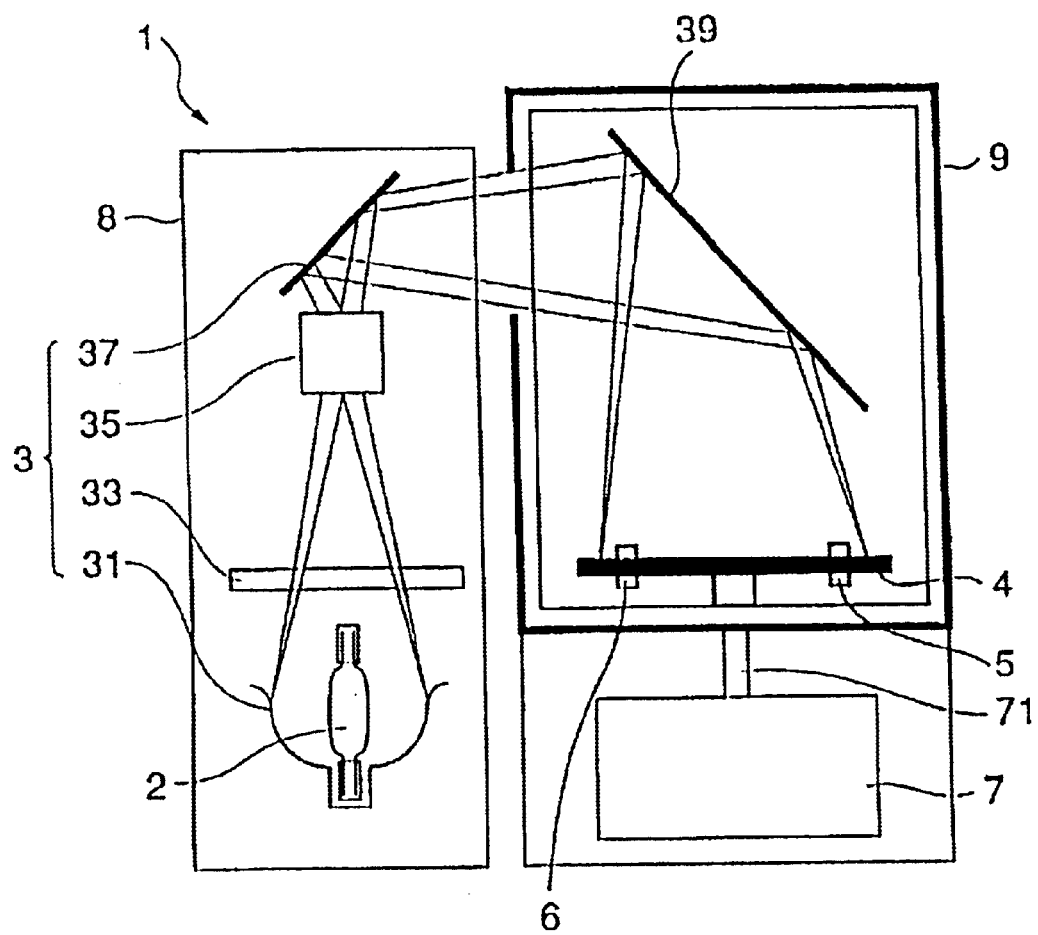
FIG. 8 is a front view showing a main part of the first light stability testing device according to the prior art.
Figure 9:
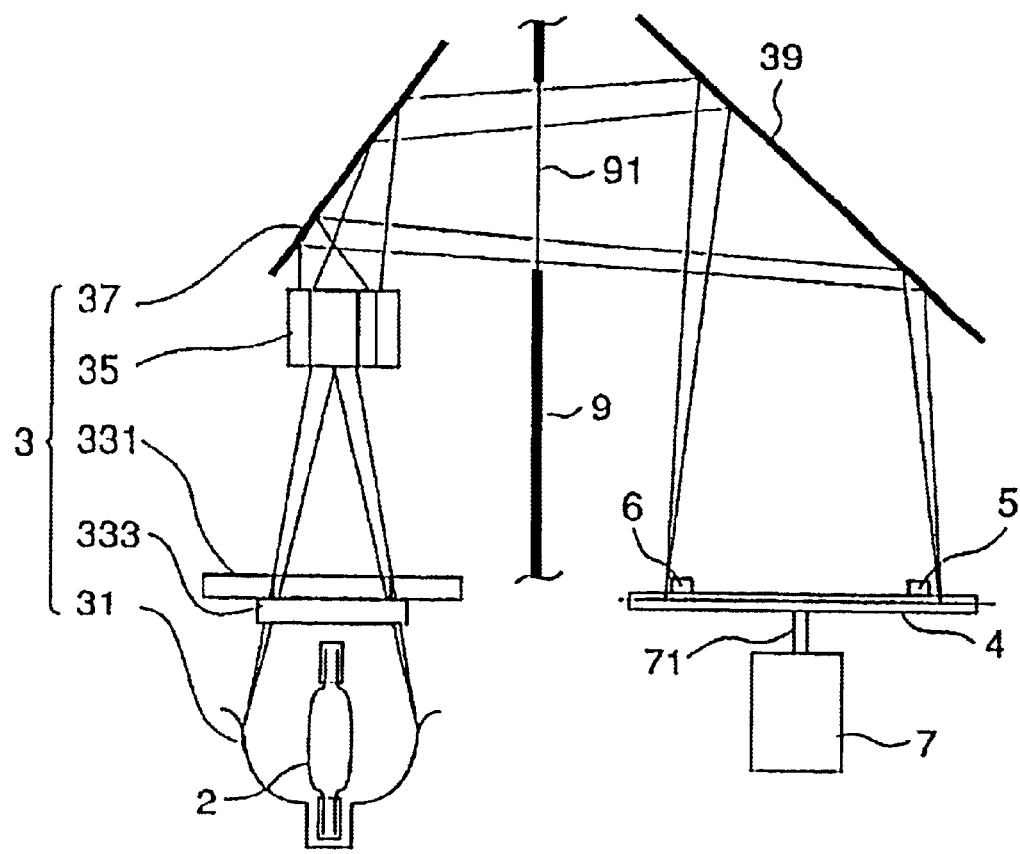
FIG. 9 is a front view showing a detailed main part of the first light stability testing device according to the prior art.

In addition, control methods of the light sources 2 include flashing control by inverter light control as shown in FIG. 7(a), flashing control by phase control as shown in FIG. 7(b), and flashing control by relatively long timing as shown in FIG. 7(c).

In addition, in the control unit, not merely by performing control based on only an instantaneous value of a signal from the sensor but also by performing control while correcting the instantaneous value in consideration of an integrated irradiation value, a further accurate light stability test becomes possible.

As described above, a light stability testing device according to the present invention enables an accurate ultraviolet irradiation and an accurate visible light irradiation, and thus can conduct an accurate light stability test.

What is claimed is:

1. A light stability testing device comprising: a light source; an optical system for regulating light rays emitted from this light source; a sample stage for placement of a sample onto which light rays passed through this optical system are to be irradiated; a light measuring sensor for measuring the dose of light rays, attached to this sample stage; and a control unit to which a signal from this light sensor is transmitted and which controls said optical system, wherein said light sensor comprises a visible light measuring sensor for measuring the dose of visible light and an ultraviolet measuring sensor for measuring the dose of ultraviolet rays, said optical system comprises a total light regulating means for regulating the absolute quantity of light rays emitted from said light source and an ultraviolet regulating means for regulating the dose of ultraviolet rays of light rays, and said control unit comprises a total light control portion for controlling said total light regulating means by a signal from said visible light measuring sensor and an ultraviolet control portion for controlling said ultraviolet regulating means by a signal from said ultraviolet measuring sensor.

2. A light stability testing device as set forth in claim 1, wherein said optical system comprises a light ray sorting means for differentiating a course of ultraviolet rays from a course of visible light and a light ray merging means for merging ultraviolet rays with visible light, and said ultraviolet regulating means regulates the dose of ultraviolet rays passed through said light ray sorting means.

3. A light stability testing device as set forth in claim 2, wherein said light ray sorting means is a dichroic mirror.

4. A light stability testing device as set forth in claim 2, wherein said light ray merging means is a dichroic mirror.

5. A light stability testing device as set forth in claim 1, wherein said total light regulating means comprises a plurality of movable filters.

6. A light stability testing device as set forth in claim 5, wherein said plurality of filters are two filters and symmetrically movable.

7. A light stability testing device as set forth in claim 1, wherein said optical system comprises a light flux control means for controlling a light flux of light rays.

8. A light stability testing device as set forth in claim 7, wherein said light flux control means is an integrated lens.

9. A light stability testing device as set forth in claim 7, wherein said ultraviolet regulating means is provided at a position to regulate the dose of ultraviolet rays of light rays passed through said light flux control means.

10. A light stability testing device as set forth in claim 1 wherein said sample stage is rotatable.

11. A light stability testing device as set forth in claim 10, wherein small rotatable sample stages are provided on said sample stage.

12. A light stability testing device as set forth in claim 11, wherein a rotation rate between said sample stage and small sample stages is 7 or more.

13. A light stability testing device as set forth in claim 1, wherein for control in the control unit, provided is a corrective control portion which corrects an instantaneous irradiation value of a signal concerning irradiation from said light sensor while taking an integrated irradiation value into consideration.

14. A light stability testing device comprising: a light source; an optical system for regulating light rays emitted from this light source; a sample stage for placement of a sample onto which light rays passed through this optical system are to be irradiated; a light measuring sensor for measuring the dose of light rays, attached to this sample stage; and a control unit to which a signal from this light sensor is transmitted and which controls said optical system, wherein said light sensor comprises a visible light measuring sensor for measuring the dose of visible light and an ultraviolet measuring sensor for measuring the dose of ultraviolet rays, said optical system comprises a total light regulating means for regulating the absolute quantity of light rays emitted from said light source and an ultraviolet regulating means for regulating the dose of ultraviolet rays of light rays emitted from this total light regulating means, and said control unit comprises a total light control portion for controlling said total light regulating means by a signal from said visible light measuring sensor and an ultraviolet control portion for controlling said ultraviolet regulating means by a signal from said ultraviolet measuring sensor.

15. A light stability testing device comprising: a light source; a sample stage for placement of a sample onto which light rays emitted from this light source are to be irradiated; a light sensor for measuring the dose of light rays, attached to this sample stage; and a control unit to which a signal from this light sensor is transmitted and which controls said light source, wherein said light source comprises excessive ultraviolet light sources and insufficient ultraviolet light sources.

16. A light stability testing device as set forth in claim 15, wherein said light sensor comprises a visible light measuring sensor for measuring the dose of visible light and an ultraviolet measuring sensor for measuring the dose of ultraviolet rays, an ultraviolet regulating means for regulating the dose of ultraviolet rays of light rays emitted from said light source is provided between said light source and sample stage, and said control unit comprising a light source control portion for controlling said light source by a signal from said visible light measuring sensor and an ultraviolet control portion for controlling said ultraviolet regulating means by a signal from said ultraviolet measuring sensor.

17. A light stability testing device as set forth in claim 16, wherein control in said light source control portion is performed by flashing control through inverter light control of said light source.

18. A light stability testing device as set forth in claim 15, wherein control in said light source control portion is performed by flashing control through phase control of said light source.

19. A light stability testing device as set forth in claim 15, wherein said light sensor comprises a visible light measuring sensor for measuring the dose of visible light and an ultraviolet measuring sensor for measuring the dose of ultraviolet rays, said control unit comprises an insufficient ultraviolet light source control portion for controlling said insufficient ultraviolet light sources by a signal from said visible light measuring sensor and an excessive ultraviolet light source control portion for controlling said excessive ultraviolet light sources by a signal from said ultraviolet measuring sensor.

* * * * *